United States Patent [19]
Schultz

[11] Patent Number: 5,403,497
[45] Date of Patent: Apr. 4, 1995

[54] NEW METHOD FOR DETERMINING PARTICLE SIZE AND CONCENTRATION IN A FLUID MEDIUM

[75] Inventor: John E. Schultz, Mount Hamilton, Calif.

[73] Assignee: Regents of the University of California, Oakland, Calif.

[21] Appl. No.: 120,291

[22] Filed: Sep. 13, 1993

[51] Int. Cl.6 .............................................. B01D 17/12
[52] U.S. Cl. .................... 210/745; 73/61.63; 73/865.9; 210/96.1; 436/10; 436/164
[58] Field of Search ......... 210/94, 96.1, 96.2, 210/745; 73/61.63, 86.59; 356/441, 442, 410, 409; 436/10, 38, 164; 422/82.05

[56] References Cited

U.S. PATENT DOCUMENTS

| | | | |
|---|---|---|---|
| 1,859,035 | 5/1932 | Hall | 356/441 |
| 2,361,235 | 10/1944 | Pick | 210/96.1 |
| 3,505,876 | 4/1970 | Niebergall | 73/865.9 |
| 5,135,662 | 8/1992 | Ho | 210/745 |

OTHER PUBLICATIONS

Publication by John L. Cleasby "Turbidimetric Control of Filter Effluent Quality", Journal of AWWA Nov. 1960 pp. 1411-1415.

"Evaluation of Particle Counting as a Measure of Treatment Plant Performance", by E. A. Hargesheimer et al., pp. 45, 66 and 67, published by the AWWA Research Foundation in 1992.

*Primary Examiner*—Joseph W. Drodge
*Attorney, Agent, or Firm*—Phillips, Moore, Lempio & Finley

[57] ABSTRACT

A method for monitoring water filter performance and efficiency, by correlating particle size and distribution to turbidity measurement. The method includes the steps of installing and calibrating the filter system, and periodically testing the filter system efficiency. The calibration of the filter system includes the step of preparing a calibration "challenge" solution having a predetermined count of particles of known size which will serve as "surrogates" for the particles which are to be removed during normal filtration. The turbidity of the calibration challenge solution is measured, and correlated to the particle count information. Similarly, the effluent turbidity is measured and a particle size distribution count made to verify the percent removal specified.

21 Claims, 11 Drawing Sheets

NEW METHOD FOR DETERMINING PARTICLE SIZE AND CONCENTRATION IN A FLUID MEDIUM

BACKGROUND OF THE INVENTION

The present invention relates in general to methods for determining the particle size and concentration in a fluid medium, and more particularly, it relates to a method for monitoring water filter performance and efficiency.

One of the major problems facing the water treatment industry today, is to determine the size distribution and concentration of particles in a water sample. A recent scientific review of the literature, relating to the evaluation of the performance of treatment plants, by means of particle counting, is published in "Evaluation of Particle Counting as a Measure of Treatment Plant Performance", by E. A. Hargesheimer et al., published by the AWWA Research Foundation in 1992.

To briefly summarize the conventional approaches listed in this publication, there are basically two general conventional ways to address the foregoing problem. The first and older approach, is referred to as the sedimentation rate study. This method includes sampling the water, and letting it settle for a certain period of time, for example one hour. Since larger particles tend to settle faster than smaller particles, the first sedimentation is made exclusively of larger particles. These particles are counted, and the water sample is allowed to settle for another period of time.

A second sedimentation, which includes smaller particles is similarly analyzed for particle concentration, and the above process of settling and counting is repeated until the desired particles of desired size are reached and counted. The use of the sedimentation rate study is no longer widely used, and is almost exclusively limited to specific applications. This approach is tedious, time consuming, and requires highly trained technical staff to count and to measure the size of each range of particles using a microscope.

The second approach is to electronically count the particles of particular sizes, within a sample, using such advanced technology as laser beams. However, this approach requires expensive counting equipment, highly trained personnel to operate and maintain the equipment. Additionally, this test takes a long time to implement in a laboratory environment.

While the conventional approaches have met with varying degrees of success in evaluating the water quality, the cost and complexity of the tests do not permit their widespread accessibility, particularly to smaller water treatment plants. This limited accessibility presents serious hinderance to the compliance with the federal and state laws, rules and regulations pertaining to water treatment standards.

On page 67 of the foregoing publication, the authors concluded that it "is not logical to seek a conversion factor to relate results from particle counting and turbidity since the level of discernment attainable by both methods is not comparable."

New laws are being continuously legislated to set water treatment and environment standards, and are becoming increasingly more stringent, due to the rising incidents of serious illnesses and deaths resulting from toxic suspended particles in water. Of special current concern are viruses and amoebic cysts, such as those of giardia and cryptosporidium.

The size of these viruses and cysts is in the order of 4 microns. Removal, and specially verification of such removal of particles of this size is expensive and has, so far, required special apparatus and trained personnel. Since the detection of viruses and cysts in very low concentrations is difficult and expensive, the rules "presume" that certain long standing technologies reduce the biological contaminants as required.

While large water treatment plants are presumed to comply, smaller treatment plants do not have the ready capability to evaluate the contamination problem, and consequently to comply with the new laws. One technology that could be used by small treatment plants is "slow sand filters". However, this alternative is still quite expensive, and requires highly trained, qualified and certified operators to conduct the tests.

Another type of filtration system that is commonly available at homes, is the "cartridge/bag filter", which is relatively inexpensive to operate and maintain. However, this type of filtration system presents its own concerns. To name a few, even if the cartridge bag filter is efficient in removing the undesirable particles, such as viruses and cysts, a leak somewhere in the water delivery system could render the filtration process futile.

One way to test the water delivery system, as a whole, would be to have a microbiologist determine the filter efficiency, by "spiking" the supply with the organisms to be removed.

Another way would be to have a specialist "challenge" the filter with four-micron size particles which serve as "surrogate" for the materials to be removed then to count the particles in the effluent to verify the required removal efficiency.

To that end, it would be highly desirable to have a new method for determining the filter efficiency. This method should be simple, inexpensive, readily accessible to permit compliance with the laws, and which would not require highly trained technical operators.

SUMMARY OF THE INVENTION

It is therefore an object of the present invention to address the foregoing concerns, and to provide adequate solutions thereto.

It is another object of the present invention to teach a new, simple, and relatively inexpensive field testing method for monitoring the water filter performance and efficiency, by providing an indirect indication of the size, distribution and concentration of the particles in the effluent.

It is yet another object of the present invention to describe a new measurement method which does not require highly trained technical personnel to operate and maintain.

Briefly, the above and further objects of the present invention are realized by a method for monitoring the water filter performance and efficiency, by correlating the particle size, concentration and distribution to turbidity measurement. The method includes the steps of installing and calibrating the filter system, and periodically testing the filter system efficiency.

The calibration of the filter system includes the step of preparing a calibration "challenge" solution having a predetermined count of particles of known composition. The turbidity of the calibration challenge solution is measured, and correlated to the particle count information. Similarly, the effluent turbidity is measured and a particle size distribution count made to verify the percent removal specified.

The testing of the filter system includes the step of preparing a test challenge solution, of the same concentration as the calibration challenge solution, by mixing a predetermined volume of a fluid medium with a specific grit including a known composition of particles.

The test challenge solution is then passed through a filter and the turbidity of the resulting effluent measured. If the turbidity "rise" of the test effluent is as low as, or lower than the turbidity "rise" of the calibration effluent, then the filter system is considered to have the required efficiency.

Further, the ambiguity inherent in inferring particle size distribution from a one-dimensional measurement, such as turbidity, can be additionally reduced, by introducing a percentage of the challenge solution into the filtered effluent, thereby having a direct indication of the turbidity associated with the actual operating conditions at the time of the test.

The present invention presents a simple process for periodic testing of the filter efficiency, in the field, under actual operating conditions. The correlation between turbidity and filter efficiency, can be periodically checked by laboratory particle counting techniques.

Additionally, the field test itself can be calibrated for internal consistency during each routine test, thereby reducing the influence of unknown changes, or uncertainties in the operating and testing conditions.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENTS

Figure 1:
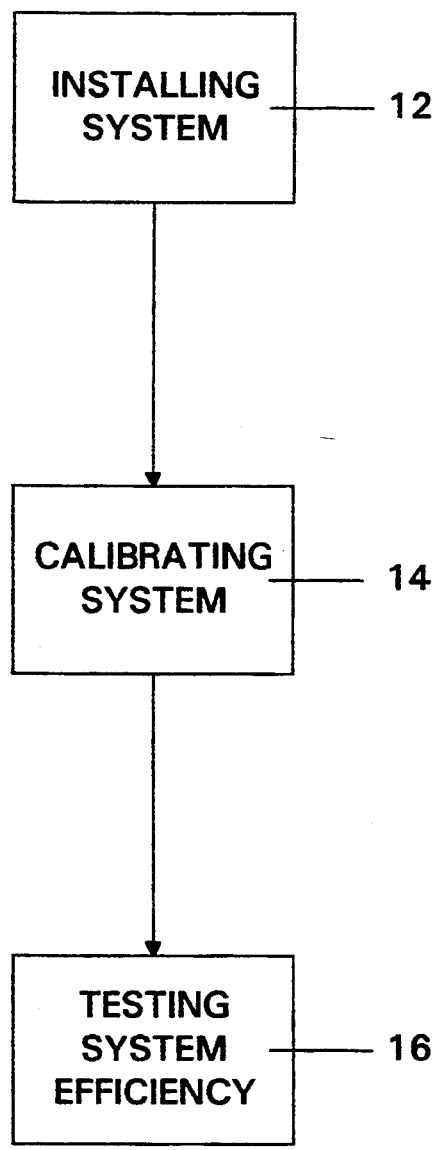
FIG. 1 is a high level block diagram of a method for determining the particle size and concentration in a fluid medium, according to the present invention.

Referring now to the drawings, and more particularly to FIG. 1 thereof, there is illustrated a new method 10 for determining the particle size and concentration in a fluid medium, according to the present invention. By using a challenge solution, turbidity measurement can be correlated to particle count information, thereby achieving indirect indication of particle distribution and filter efficiency.

As used herein, the terms "challenge solution" mean a solution containing particles of known size and concentration.

The term "turbidity" refers to the clarity of the fluid medium, such as water. Turbidity interferes with the transmission of a light beam through the fluid medium. As the number of suspended particles increases, the turbidity increases, and causes increased interference with light transmission and increased "scattering" of light.

Figure 4:
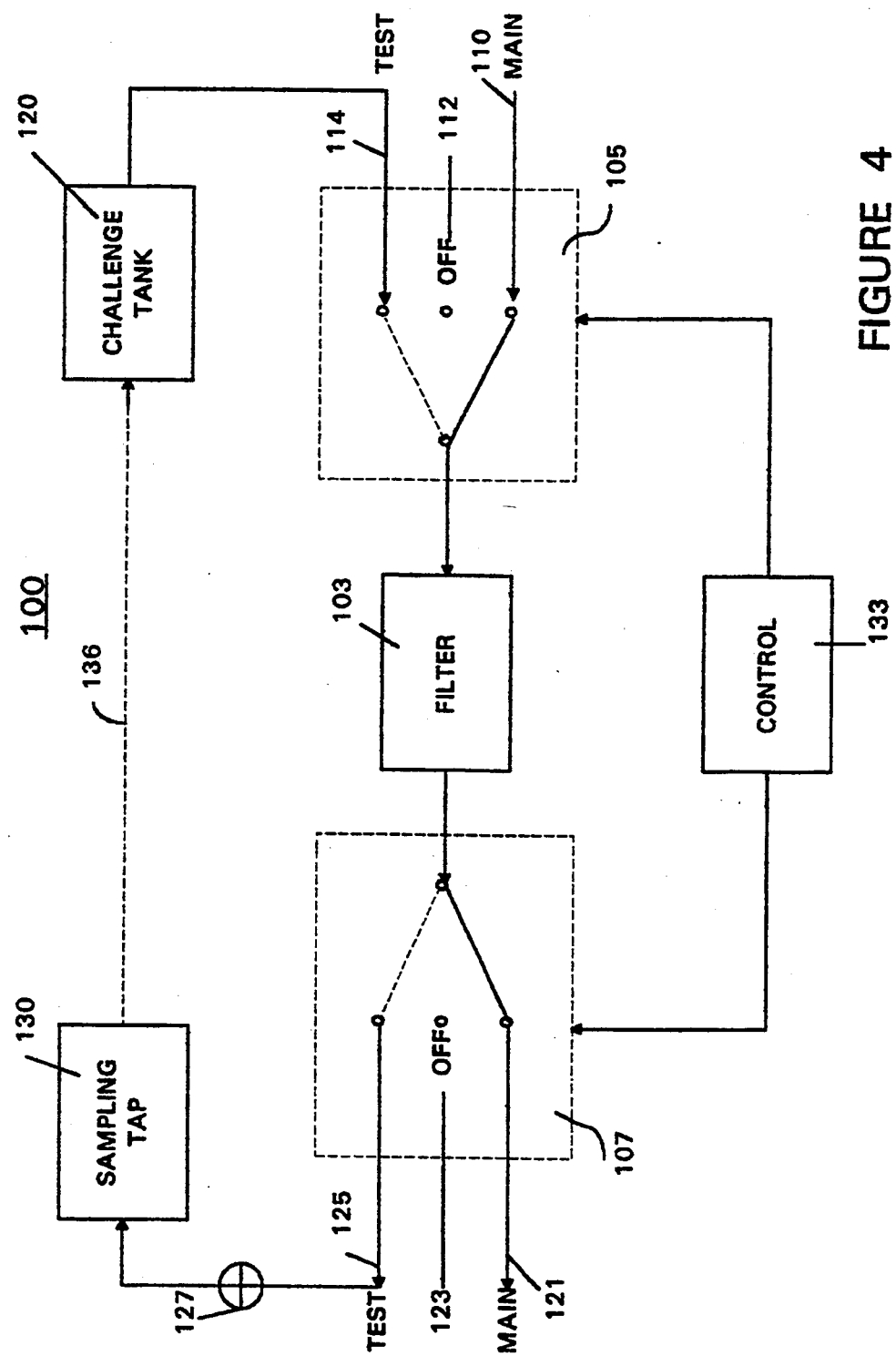
FIG. 4 is a block diagram of the filter system for implementing the processes illustrated in FIGS. 1 through 3.
Figure 8:
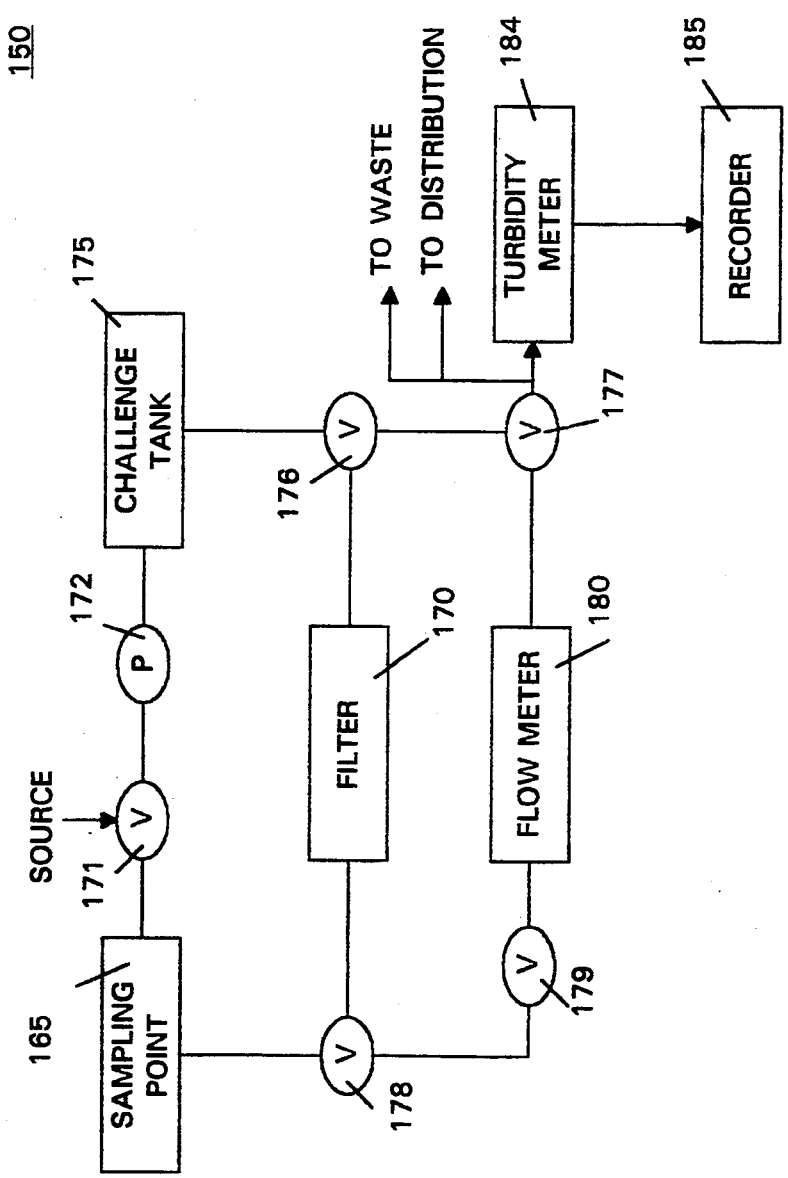
FIG. 8 is a block diagram of the filter system for implementing the processes illustrated in FIGS. 5A through 7.

The method 10 generally includes the step of installing a filter system, such as the filter system 100, which is illustrated in FIG. 4, or the filter system 150, which is illustrated in FIG. 8. The installation step is indicated by block 12. The filter system (100 or 150) is then calibrated and tested, as indicated by blocks 14 and 16, respectively. Each of these steps 12, 14 and 16 will now be described in greater detail, first in connection to the filter system 100, and then in connection to the filter system 150.

The installation (block 12) of the filter system 100 includes the step of fluidly connecting the components of the system 100, as shown in FIG. 4. The system 100 comprises a filter 103 which is connected between an inflow three-way valve 105, and an outflow three-way valve 107.

The inflow valve 105 includes three positions. The first position is the MAIN or SOURCE position 110, which allows the source fluid, such as water, to flow to the filter 103. An OFF position 112 disconnects the filter system 100 from the inflow of fluid. A TEST position 114 connects the filter 103 to a challenge tank 120, which contains the challenge solution.

The outflow valve 107 similarly includes three positions. The first position is the MAIN position 121, which connects the filtered water to an external distribution system (not shown). An OFF position 123 disconnects the filter 103 from the external distribution system. A TEST position 125 connects the filtered water to a pump 127, which draws the filtered water to a sampling point, tank or tap 130, and optionally back to the challenge tank 120, along the transmission path or line 136.

While in the preferred embodiment, the inflow and outflow valves 105 and 107 are actuated manually, it should be understood to those skilled in the art, after reviewing the present specification, that a control circuit 133 could be added to regulate the function of the inflow and outflow valves 105 and 107, and of the flow of water passing therethrough.

Figure 2:
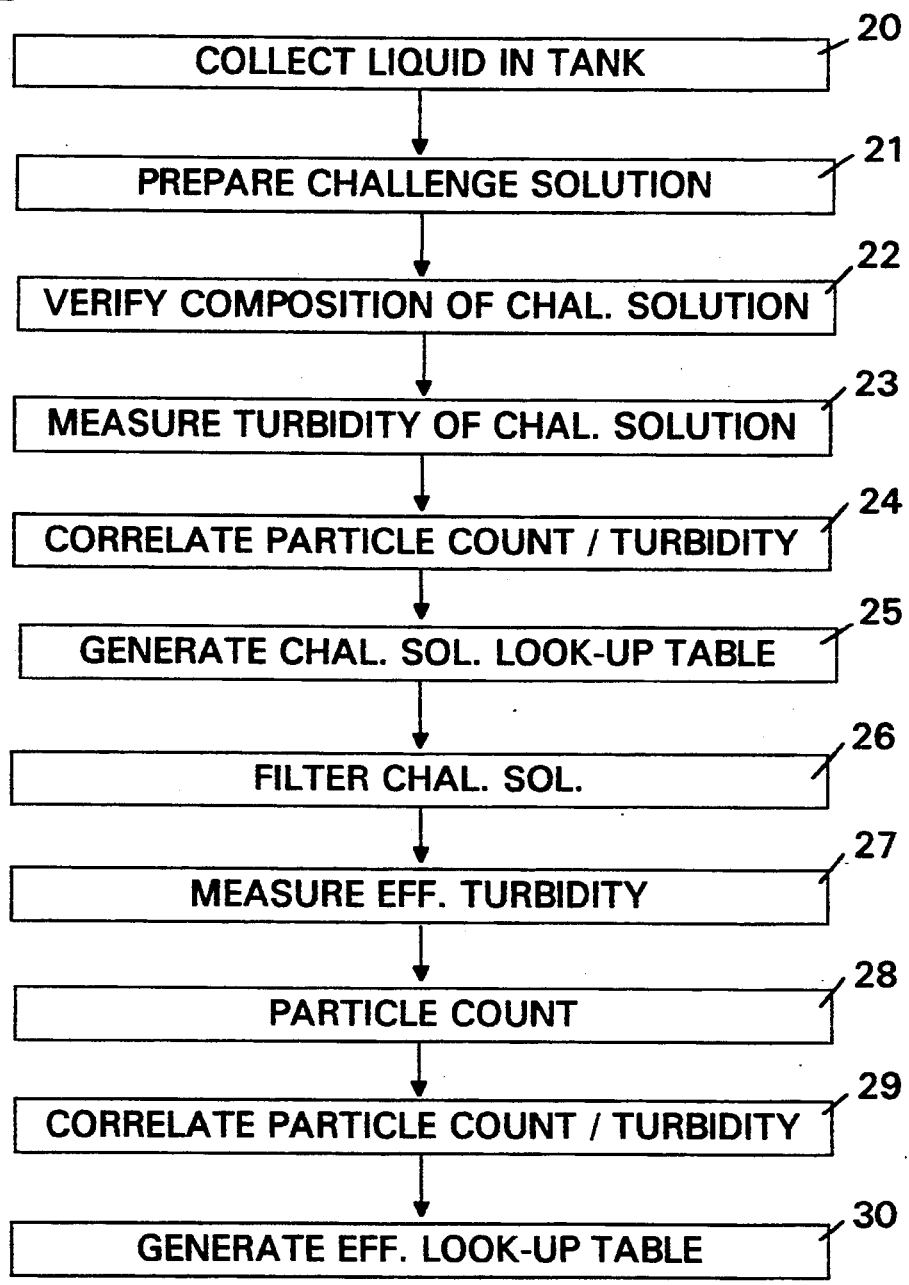
FIG. 2 is are block diagram illustrating a first process for calibrating a filter system, which forms a part of the inventive method of FIG. 1.
Figure 3:
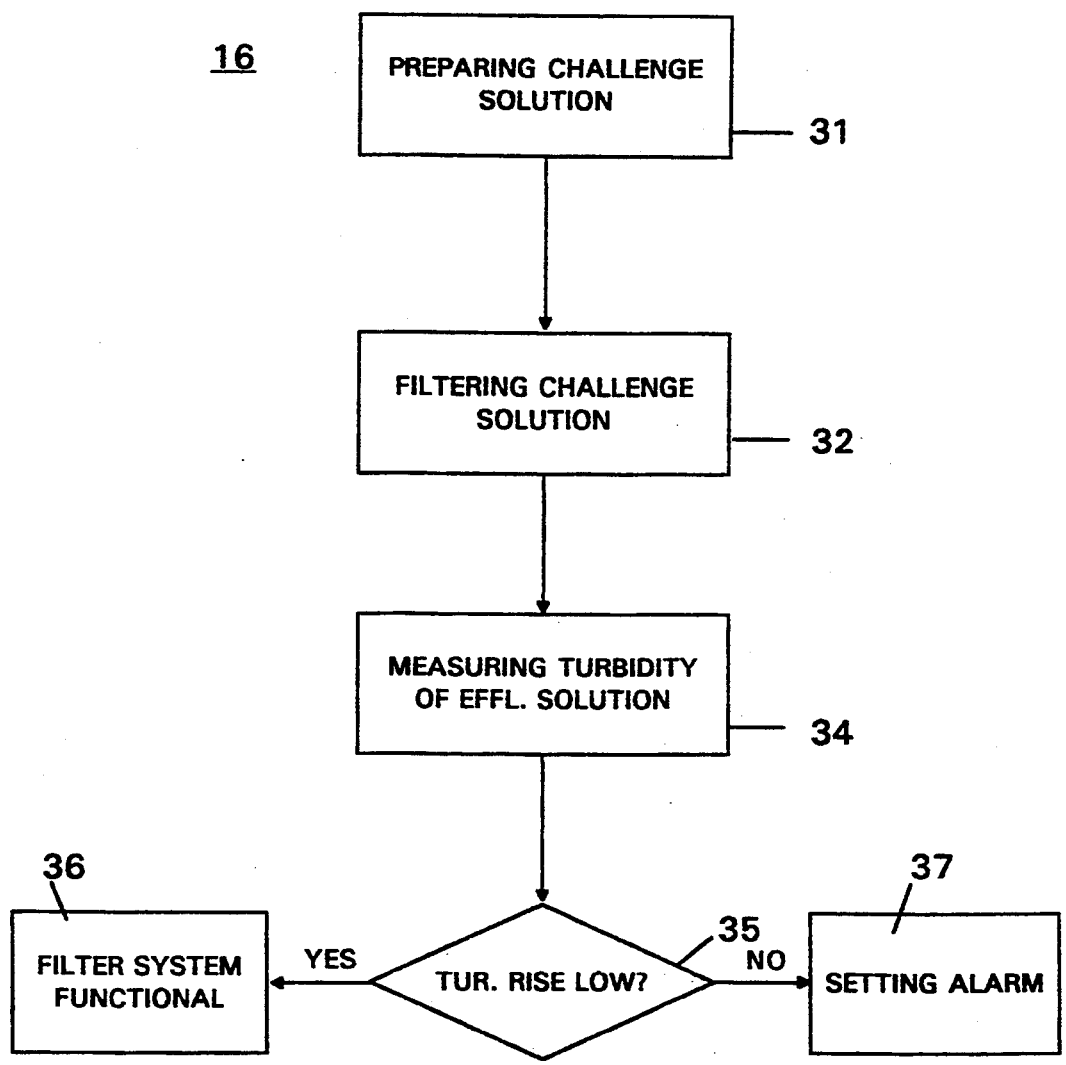
FIG. 3 is a block diagram illustrating a first process for testing the filter system, which forms a part of the method of FIG. 1.

The control circuit 133 is connected to the inflow and outflow valves 105 and 107, and regulates the operation of the pump 127. The control circuit 133, could be a personal computer (PC), which includes a CPU, a ROM and a RAM, where a software program is stored and executed. The control circuit 133 may also be used to cause the filter system 100 to automatically implement the calibration step 14, and to periodically conduct the testing step 16, as illustrated in FIGS. 2 and 3, respectively.

The calibration process 14 of the filter system 100 will now be described in connection with FIG. 2. The calibration process 14 is carried out by collecting water into the challenge tank 120, as shown in block 20. The three-way valves 105 and 107 are connected to the TEST positions 114 and 125, respectively, and the pump 127 causes the water in the challenge tank 120 to flow through the filter 103, to the sampling tap 130, where a sample of the "effluent" (i.e., filtered challenge solution) is taken.

In the preferred embodiment of the present invention, the water at the outlet of the sampling tap 130 is redirected to the challenge tank 120, along the transmission path 136, which is represented by a dashed line. In other applications, the water forming the initial challenge solution is supplied directly from the main source 110.

The challenge solution is then prepared (block 21), by adding a grit of known composition to the water collected in the challenge tank 120. The grit contains particles of predetermined sizes, and concentration. An exemplary challenge solution contains 200 grams of grit to 100 gallons of water.

The calibration method 14 further includes the step of verifying the composition of the challenge solution, by counting the particles of particular size ranges of interest, which are expected to be removed by the filter 103. This verification step is illustrated by block 22.

The turbidity of the challenge solution is then measured, as indicated by the block 23, and correlated to the concentration of the various counts of particle sizes, as indicated by the block 24. It should be understood that the absolute measured turbidity may vary with changes, especially seasonal, in the source water. A corresponding challenge solution look-up table is then generated, as indicated by the block 25. The data in the look up table could be stored in the control circuit 133, for future correlation and testing.

The challenge solution prepared at step or block 21, is then passed through the filter 103, as indicated by block 26. The effluent turbidity is then measured at 27, and the particle count done at 28. The particle count is then correlated to the measured effluent turbidity (block 29), and a corresponding effluent look-up table is generated at block 30.

The "rise" in turbidity is the difference between the turbidity of the challenge solution, as measured in block 23, and the effluent turbidity, as measured in block 27. Focusing on turbidity rise, rather than absolute value essentially compensates for source water variations.

The particle count reflects the efficiency of the filter system 100. Thus, the present method 10 could be used to determine the particle removal or introduction efficiency of a water transmission system or part(s) thereof, which do not necessarily include a filter.

It should be understood that, while only one sampling count is disclosed, additional samples challenge solution could be taken and the particles counted, in the manner described above. The turbidity of these additional samples will be measured and correlated to the particle counts, as part of the look-up table These additional samples could be obtained by causing the challenge solution to be filtered for the first time, as described above. The filtered solution is then routed to sampling tank 130, where it stored until all the challenge solution in the challenge tank 120 is filtered by the filter 103. Thereafter, the solution in the sampling tank 130 is circulated to the challenge tank 120, and then through the filter 103, to be stored once again in the sampling tank 130.

The stored solution is sampled and its turbidity correlated to the particle counts, as explained above. The foregoing steps are repeated as many times as needed, and the data entered in the look-up table.

Upon completion of the calibration of the filter system 100, periodic testing is required, to insure its proper operation, and compliance with regulations. The periodic tests could be carried out either manually, or automatically by the control circuit 133. FIG. 3 illustrates the steps of an exemplary test process 16.

The first step in the process 16 is to prepare the challenge solution (block 31), of the same concentration as the calibration challenge solution, by mixing a predetermined volume of filtered water with a specific grit including a known composition of particles.

Optionally, the turbidity of the challenge solution is measured, and by using the challenge solution look up table, which has already been prepared during the calibration process 14, it is now possible to correlate the turbidity of the challenge solution to the count of particles contained therein. The correlation step is expedient, convenient, simple, inexpensive, and does not require the assistance of a trained particle count specialist.

In practice, for the routine testing of a small water system, the test challenge solution will be prepared each time, by the addition of a specified quantity of the challenge grit to a predetermined volume of filtered source water in the challenge tank 120, without the need to verify the turbidity of the challenge solution.

The three-way valves 105 and 107 are switched to the TEST positions 114 and 125, respectively, and the challenge solution is pumped through the filter 103, as indicated by the block 32. The resulting effluent or filtered challenge solution is then sampled at the sampling tap 130, and its turbidity measured at block 34, and compared to the effluent look-up table (block 35), which has already been prepared during the calibration process 14.

If the "rise" in the turbidity (as defined previously), of the resulting test effluent were found to be as low as, or lower than the "rise" in the turbidity of the calibration effluent (shown in the effluent look-up table), then the filter system 100, or more specifically the filter 103, is considered to have the required efficiency, as indicated by block 36.

If on the other hand, the measured turbidity rise of the test effluent is not within acceptable parameters, i.e. it is greater than the turbidity rise of the calibration effluent, then an alarm is set, and appropriate corrective actions, such as replacing the filter 103 or maintaining the filter system 100, would be required.

The turbidity data is added to the look-up tables and labeled test, to distinguish it from the calibration data, since, when the filter is eventually replaced or cleaned, the data associated with a particular filter could be discarded, or retained for records or statistical and experimentation purposes.

In certain applications, if the system 100 does not require elaborate and frequent testing, the calibration process 14 might not require look-up tables to be generated, i.e. the steps illustrated by block 25 and 30, in FIG. 2, are omitted. Consequently, when conducting the test process 16, the test effluent turbidity measurement, obtained at step 34, is compared to the calibration effluent turbidity measurement, which was measured at step 23 of FIG. 2.

If the turbidity of the test effluent were found to be as low as, or lower than the turbidity of the calibration effluent, then the filter system 100 is considered to have the required efficiency, as indicated by block 36. Otherwise, the filter system 100 is not operating properly, and corrective actions are required.

In other embodiments of the inventive test procedure 10, two or more different calibration solutions could be used, to determine an "acceptable range" of turbidity measurement.

Figure 5A:
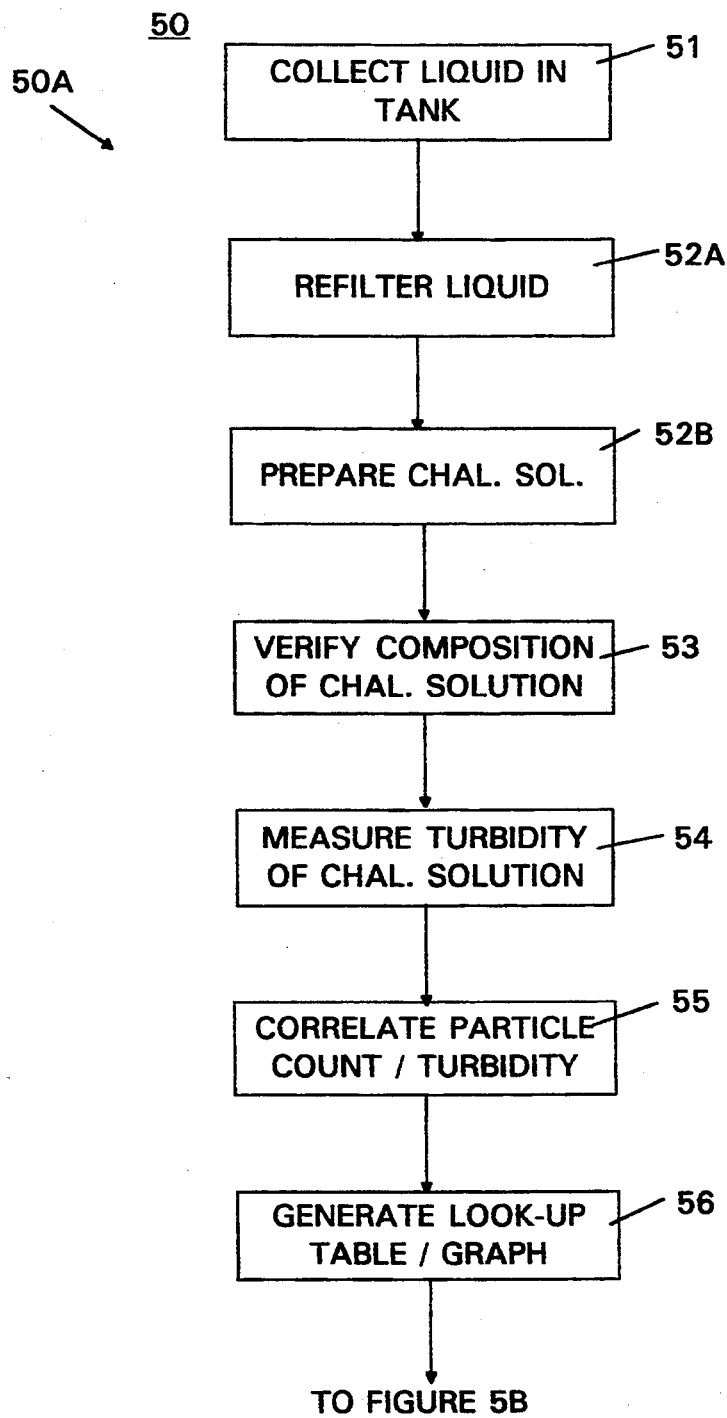
FIGS. 5A, 5B and 5C are block diagrams illustrating a second process for calibrating another filter system (FIG. 8), which forms a part of the method of FIG. 1.
Figure 5B:
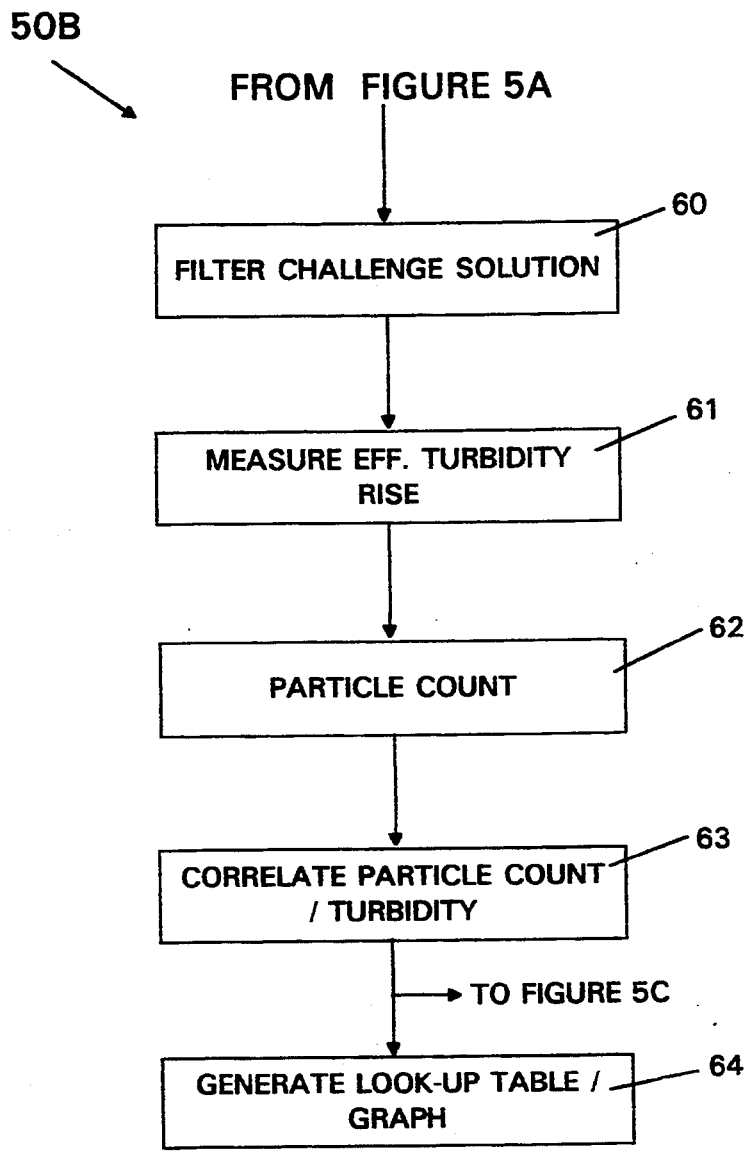
Figure 5C:
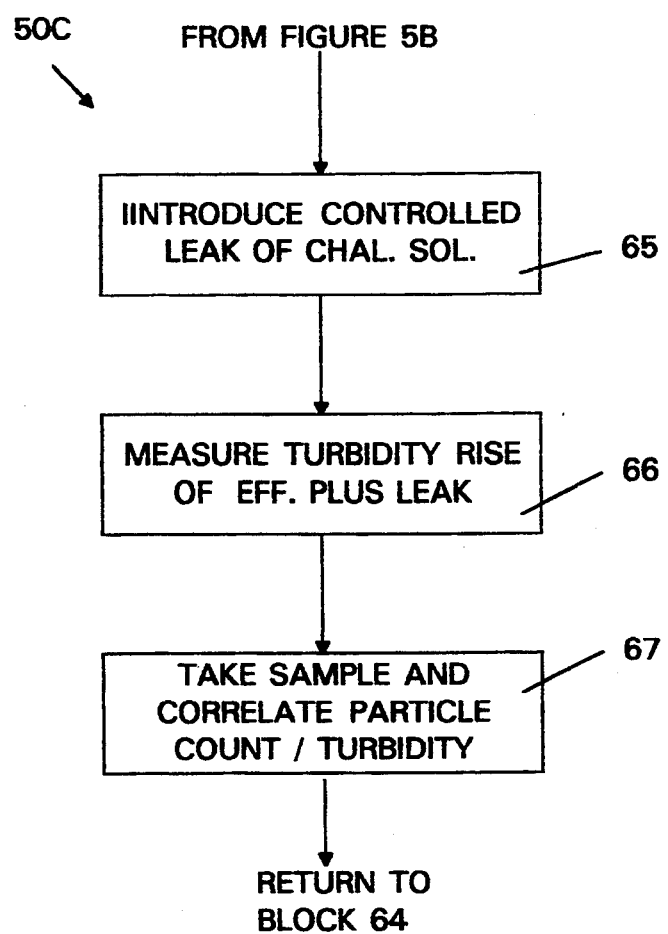
Figure 6A:
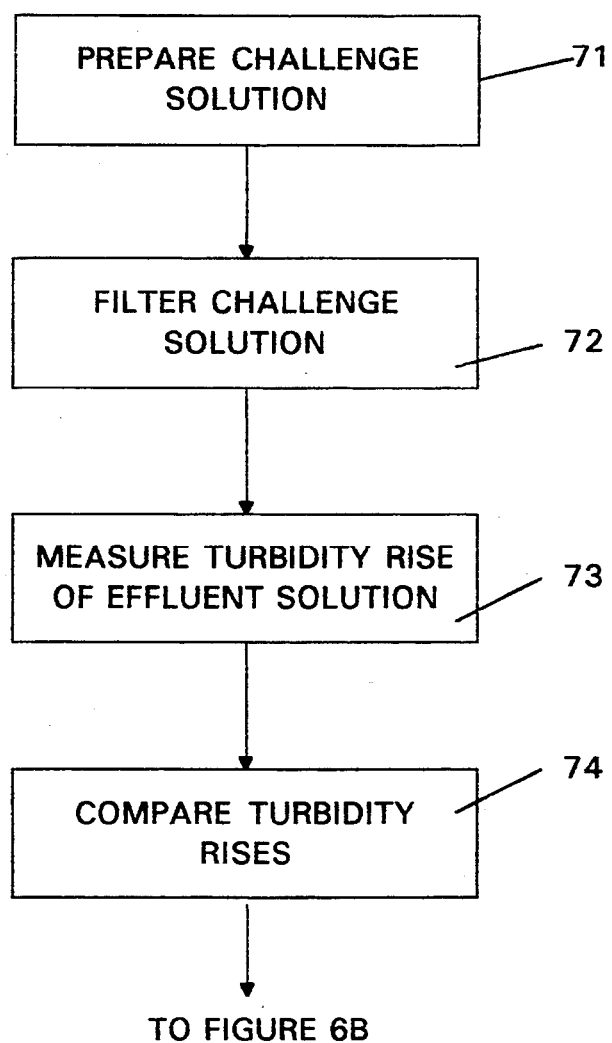
FIGS. 6A and 6B are block diagrams illustrating a second process for testing the filter system of FIG. 8, which forms a part of the inventive method of FIG. 1.
Figure 6B:
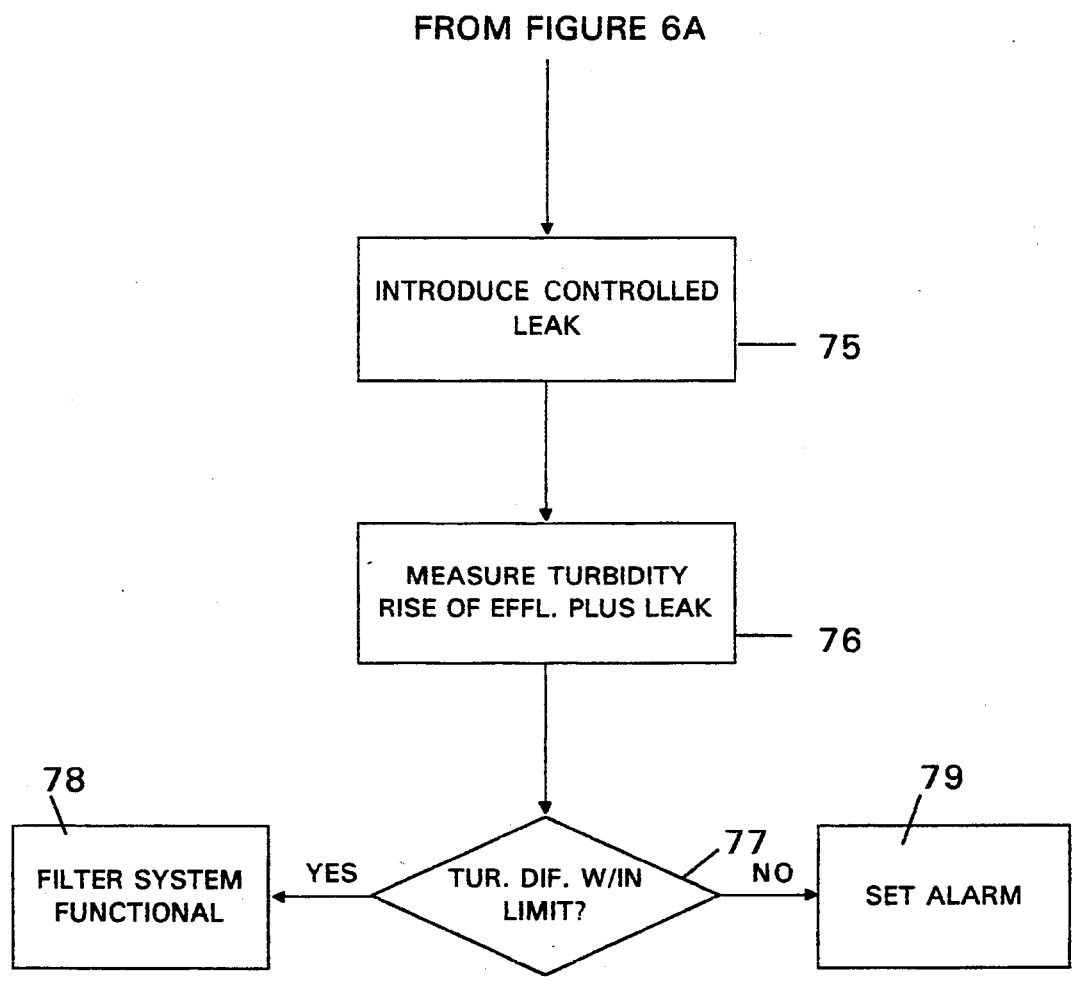
Figure 7:
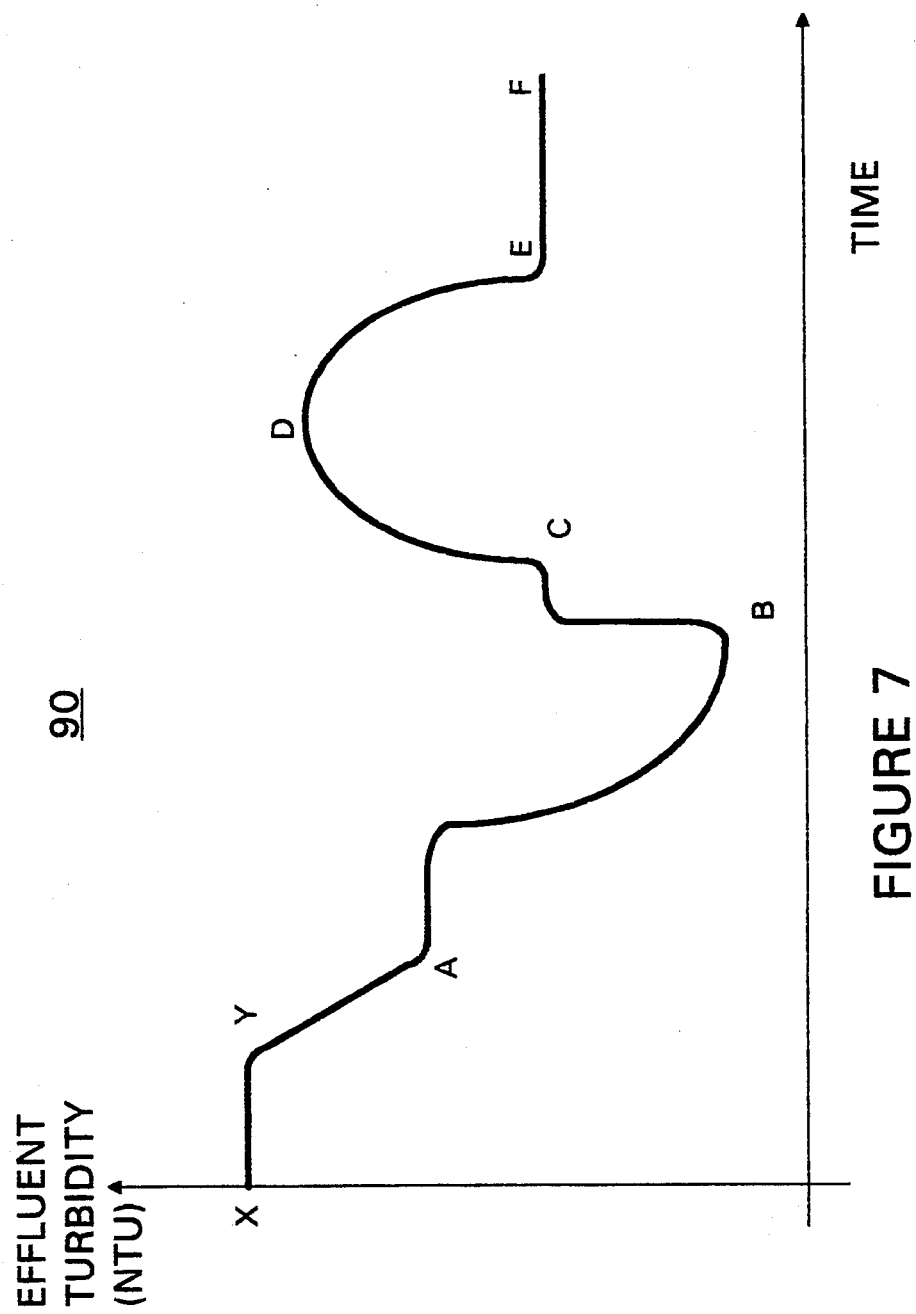
FIG. 7 is a graph showing the effluent turbidity measurement versus time, using the method of FIG. 1.

The inventive method 10 will now be described in more details, in connection with FIGS. 5A through 8. FIGS. 5A, 5B and 5C are block diagrams illustrating a process 50 for calibrating the filter system 150 of FIG. 8. FIGS. 6A and 6B are block diagrams illustrating a process 70 for testing the filter system 150. FIG. 7 is a graph 90 showing the effluent turbidity measurement versus time.

Starting with FIG. 8, it shows a block diagram of the filter system 150, for implementing the calibration process 50 and the testing process 70 illustrated in FIGS. 5A through 6B.

The installation (block 12) of the filter system 150 includes the step of fluidly connecting the components of the system 150, as shown in FIG. 8. The system 150 comprises a filter 170 which is connected between valves 178 and 176. The valve 176 allows the challenge solution in a challenge tank 175, to be selectively, fluidly connected to the filter 170.

The challenge tank 175 is also connected to the fluid source, via a three-way valve 171. A sampling point or tap 165 is connected between the three-way valve 171 and the valve 178. Under normal operating conditions, the challenge tank 175 is not connected to the filter 170, and the source water flows through the valve 171, the sampling point 165, the valve 178, the filter 170, the valve 176, and then, through a valve 177 for distribution.

In the preferred embodiment, a turbidity meter 184 is connected to the valve 177, for continuously measuring the turbidity of the effluent. A recorder 185 is connected to the turbidity meter 184, for storing turbidity and other related data. While not shown in FIG. 8, a controller, similar to the controller 133 of FIG. 4, could be connected to the various components of the filter system 150, for regulating and automating its operation. A flowmeter 180 and a controlled leak valve 179 are connected between the valves 178 and 177.

The initial calibration of the filter system 150, will now be described in detail, in relation to FIGS. 5A, 5B, 5C, 7 and 8. The calibration process 50 includes three sub-processes or routines 50A, 50B and 50C that are illustrated in FIG. 5A, 5B and 5C, respectively. The first sub-process 50A is illustrated in FIG. 5A, and relates to the preparation of the calibration challenge solution. The second sub-process 50B is illustrated in FIG. 5B, and relates to the filtering of the calibrated challenge solution. The third sub-process 50C is illustrated in FIG. 5C, and relates to a controlled leak simulation test.

Returning now to the first sub-process 50A, it will be described in connection with FIGS. 5A, 7 and 8. The sub-process 50A includes the steps of collecting filter effluent (source water filtered in normal mode) in the challenge tank 175, at block 51, and refiltering it until a stable turbidity is measured (block 52A). Thereafter, the calibration challenge solution is prepared at block 52, by adding known quantities of particulate matter (grit). The composition of the challenge solution is then verified at step 53, and its turbidity measured at step 54.

Further, a part of the graph 90, of FIG. 7 is also prepared, at step 56, in addition to the challenge solution look-up table. The portion X-Y of the graph 90, illustrates the turbidity measurement of the source water. For illustration purpose, the turbidity measurement at point Y is 0.13 NTU.

The portion Y-A of the graph 90, illustrates the effluent turbidity measurement of the once-through effluent being filtered, for the first time by the filter 170. The turbidity measurement drops from point Y (of the influent) to point A. Point A is referred to as the "once through effluent" point. For illustration purpose, the turbidity measurement at point A is 0.60 NTU. The turbidity of the "once-through" effluent will vary depending upon the variation in the composition of the source water and the "ripeness" of the filter.

The collected once-through effluent is allowed to recirculate through, and be refiltered by, the filter 170, until a desired turbidity measurement is reached (i.e. point B on graph 90). The portion A-B of the graph 90 illustrates a drop in the effluent turbidity, as the effluent is being refiltered. Point B is the lowest turbidity point. In other words, even if the effluent were allowed to be refiltered again, the turbidity will not decrease significantly, i.e., it will remain substantially constant.

The recirculation is carried out so as to eliminate as much background turbidity as possible, such that the turbidity difference upon challenging the filter is large relative to the initial turbidity. In other words, if the challenge solution were formed by adding the grit at point A, rather than at a later stage, such as point B (FIG. 7), the difference in turbidity would not be due only to the fraction of the challenge solution grit which is not intercepted by the filter 170, and thus appearing in the effluent.

The effluent turbidity is measured at point B (FIG. 7), as indicated by block 54 (FIG. 5A). For illustration purpose, the turbidity measurement at point B is 0.0040 NTU. The particle count is also done at point B, as indicated by block 54 (FIG. 5A). The turbidity is then correlated to the particle count (block 55), and a look up table and a part (portion X-B) of the graph 90 is then generated and stored.

The second sub-process 50B of the calibration process 50, will be described in detail, in connection with FIGS. 5B, 7 and 8. The prepared challenge solution is prepared in the tank 175 by adding grit so that the turbidity measures approximately 200 NTU. It then is pumped through the filter 170, via the valves 171, 178, 176, the pump 172 and the sampling point 165.

The calibration challenge solution is then filtered through the filter 170 (FIG. 8), as indicated by the block 60 (FIG. 5B). The effluent turbidity rise is then measured at block 61 (point C in FIG. 7) with an exemplary value of 0.050 NTU, and the particle count done at block 62.

The particle count is correlated to turbidity and turbidity rise of the effluent, at block 63, and a look-up table and part of the graph 90 are generated at block 64. The rise in the effluent turbidity under challenge is plotted as portion B-C in graph 90. For illustration, the effluent turbidity rise is 0.020 NTU, and the challenge turbidity may be approximately 200 NTU.

With the use of the recirculated effluent to make the challenge solution at point B, the ratio of the turbidity rise under challenge to the initial turbidity would be larger than if made with "once through" fluid corresponding to that at point A. For example, the turbidity rise ratio at point B is equal to 67% (0.020 NTU/0.030 NTU), compared to the turbidity rise ratio at point A which would have been 33% (0.020 NTU/0.060 NTU).

Referring now to FIG. 5C, 7 and 8, the third sub-process 50C of the calibration process 50 will be described in detail. This sub-process 50C is referred to as the simulation leak calibration method. It includes the step of introducing a controlled leak of the challenge solution at block 65, by allowing a predetermined volume of challenge solution to bypass the filter 170, via the actuation of the controlled leak valve 179 (FIG. 8).

The size of the simulated leak corresponds to the maximum permitted permeation of the challenge solution. For example, many regulations mandate three-log of reduction in giardia. Depending upon the particle counting technology used, giardia cysts maybe sensed as four (4) microns sphere equivalent. Three-log reduction implies that only one thousandth of the influent particles permeate the filter, to appear in the effluent. If one thousandth of the challenge solution is introduced as a simulated leak into the effluent, the resulting turbidity rise will be a direct indication of the maximum turbidity rise permissible under the actual conditions of the challenge test.

The turbidity rise associated with the maximum permissible permeation of particles of the size regulated, is illustrated by section C-D of the graph 90 (FIG. 8). The turbidity of the effluent plus the simulated leak (point D), and the turbidity rise (section C-D) are measured, as indicated by block 66 (FIG. 5C). A sample is then taken, and a particle count is done at block 67. A particle count/turbidity correlation is prepared and stored at block 64.

Once the simulated leak test is completed, the valve 179 is shut off, and the turbidity decrease (section D-E) is measured and graphed, as shown in FIG. 90. Thus, during initial calibration, four (4) particles counts are done. The first is for the initial source water influent at point X; the second is for the refiltered effluent, at point B; the third is for the effluent or once-through filtered challenge solution (effluent), at point C; and the fourth is for the effluent of the challenge solution plus the simulated leak, at point D.

Turning now to FIGS. 6A and 6B, there is illustrated a method 70 for periodic testing of the filter system 150. The testing process 70 is substantially similar to the calibration process 50 of FIGS. 5A, 5B and 5C, except that the four steps of counting the particles are omitted. Consequently, the steps in FIGS. 5A and 5B have been combined, for simplicity of illustration, into the steps shown in FIG. 6A.

The testing process 70 includes the steps of preparing the challenge solution (block 71), as explained above in relation to the calibration process (FIG. 5A), and passing the challenge solution through the filter 170 (block 72), as previously described in connection with block 60 (FIG. 5A). The turbidity and the turbidity rise of the effluent solution are measured at block 73. The turbidity rise schematically corresponds to the calibration turbidity rise B-C of graph 90 (FIG. 7), and will be designated by B'-C'.

At block 74 of the test process 70, the calibration and test turbidity rises B-C and B'-C', respectively, are compared for an initial indication of the working condition of the filter 170. If B'-C' were found to be smaller than, or equal to B-C, then the filter system 150 is presumed to be operating properly, i.e., to have the required efficiency. If, on the other hand, B'-C' were found to be larger than B-C, then the filter system 150 is presumed not to have the required efficiency.

While the foregoing is an adequate test of the operation of the filter system 150 in general, and the filter 170 in particular, it would be desirable to conduct an additional test, which will confirm the result obtained so far, by the above test This additional test is illustrated is FIG. 6B, and is referred to as the simulated controlled leak test.

The simulated controlled leak test is illustrated in FIG. 6B, and includes the step of introducing a controlled leak, at block 75, as discussed above in connection with block 65 of FIG. 5C. The turbidity of the effluent plus leak is measured and indicated by D', in correspondence to point D of graph 90. The turbidity rise C'-D' is also measured, and compared to the calibration turbidity rise B'-C', at block 77.

If B'-C' were found to be smaller than, or equal to C'-D', then the filter system 150 is determined to have the required efficiency (block 78), because C'-D' is the maximum allowable permeation of the size of the particles regulated. If, on the other hand, B'-C' were found to be larger than C'-D', then the filter system 150 is determined not to have the required efficiency (block 79).

Other comparative analyses of the relations between the turbidity rises B-C, B'-C', C-D and C'-D' could be used to further confirm the operation status of the filter system 150.

It should be understood to those skilled in the art, after reviewing the present specification, that the inventive method 10 could be used to test the efficiency of an portion of a filter system, without including the filter per se. For example, the filter systems 100 and 150 could consist exclusively of a portion of a distribution network, from supply, to treatment, to distribution, including pipes and valves.

The test method 10 may be used in several other applications where particle counting is practiced, and is not limited to water filter performance and efficiency. For instance, animals and cattle are subject to water borne parasites, and extensive attempts have been undertaken to control related diseases in live stocks. The test method 10 enables field testing of the water and filter efficiency, and consequently, it presents a significant advantage over the complex conventional laboratory tests.

While particular embodiments of the present invention have been disclosed, it is to be understood that various different modifications are possible and are contemplated within the scope of the specification, drawings, abstract and appended claims.

What is claimed is:

1. A method for determining the efficiency of a filter system for a fluid medium, the method comprising the steps of:
    a) installing the filter system for use under actual operating conditions;
    b) calibrating the filter system; and
    c) testing the filter system efficiency;
    d) said step of calibrating the filter system including the steps of:
        i. preparing a calibration challenge solution having a predetermined count of particles of known composition and sizes;
        ii. filtering said calibration challenge solution to generate a calibration effluent;
        iii. measuring the turbidity of said calibration effluent; and iv. correlating the measured turbidity of said calibration effluent to particle count information.

2. The method according to claim 1, wherein said step of testing includes the steps of:
   a) preparing a test challenge solution of substantially similar concentration to that of said calibration challenge solution;
   b) filtering said test challenge solution to generate a test effluent;
   c) measuring the turbidity of said test effluent;
   d) comparing the turbidity of said test effluent to the turbidity of said calibration effluent, for determining the efficiency of the filter system.

3. The method according to claim 2, wherein said step of calibrating the filter system further includes the step of verifying the composition of said calibration challenge solution, by conducting a particle count.

4. The method according to claim 3, wherein said step of calibrating includes generating a look-up table which correlates the turbidity of said calibration challenge solution to said count information.

5. The method according to claim 4, wherein said step of calibrating includes the step of preparing and processing at least one additional calibration challenge solution, and the step of correlating the measured turbidity to the particle count information is repeated according to the number of calibration challenge solutions.

6. The method according to claim 2, wherein said step of testing includes the step of verifying the composition of said test challenge solution, by correlating and comparing the turbidity of said test effluent and the turbidity of said calibration effluent.

7. The method according to claim 2, wherein, if the turbidity of said test effluent is as low as, or lower than the turbidity of said calibration effluent, then the filter system is considered to have the required efficiency.

8. The method according to claim 7, wherein the fluid medium is water.

9. The method according to claim 2, wherein said step of calibrating further includes the step of measuring the difference between the turbidity of the calibration solution and the turbidity of the calibration effluent.

10. The method according to claim 9, wherein said step of testing further includes the step of measuring the difference between the turbidity of the test solution and the turbidity of the test effluent.

11. The method according to claim 10, further including the step of comparing the difference between the turbidity of the calibration challenge solution an the turbidity of the calibration effluent to the difference between the turbidity of the test solution and the turbidity of the test effluent.

12. The method according to claim 11, wherein, if the difference in turbidity between said test solution and said test effluent is smaller than, or equal to, the difference in turbidity between said calibration solution and said calibration effluent, the filter system is presumed to have the required efficiency.

13. The method according to claim 12, wherein, if the difference in turbidity of said test effluent is greater than the difference in turbidity of said calibration effluent, the filter system is presumed not to have the required efficiency.

14. The method according to claim 11, wherein said step of calibrating further includes the step of conducting a first simulated leak, and measuring the difference in turbidity between the measured turbidity of the calibration effluent with the measured turbidity of the leak.

15. The method according to claim 14, wherein said step of testing further includes the step of conducting a second simulated leak, and measuring the difference in turbidity between the measured turbidity of the test effluent and the measured turbidity of the second simulated leak.

16. The method according to claim 15, wherein the step of testing further includes the step of comparing difference in turbidity between said test solution and said test effluent to the difference in turbidity between said test effluent and the second simulated leak.

17. The method according to claim 16, wherein, if the difference in turbidity between said test solution and said test effluent is smaller than, or equal to, the difference in turbidity between said calibration effluent and the simulated leak, the filter system is presumed to have the required efficiency.

18. The method according no claim 17, wherein, if the difference in turbidity between said test solution and said test effluent is greater than the difference in turbidity between said calibration effluent and the simulated leak, the filter system is presumed not to have the required efficiency.

19. The method according to claim 18, wherein, if the difference in turbidity between said test solution and said test effluent is smaller than, or equal to, the difference in turbidity between said calibration effluent and said second simulated leak, the filter system is presumed to have the required efficiency.

20. The method according to claim 14, wherein the step of testing further includes the step of comparing the difference in turbidity between said test solution and said test effluent and the difference in turbidity between said calibration effluent and the second simulated leak.

21. A method for determining the efficiency of a filter system for a fluid medium, the method comprising the steps of:
   a) installing the filter system; and,
   b) calibrating the filter system; and
   c) testing the filter system efficiency;
   d) said step of calibrating the filter system including the steps of:
      i. preparing a calibration challenge solution having a predetermined count of particles of known composition and sizes;
      ii. filtering said calibration challenge solution to generate a calibration effluent;
      iii. measuring the turbidity of said calibration effluent; and
      iv. correlating the measured turbidity of said calibration effluent to particle count information;
   e) wherein the step of testing the filter system includes the steps of:
      i. preparing a test challenge solution of substantially similar concentration to that of said calibration challenge solution;
      ii. filtering said test challenge solution to generate a test effluent;
      iii. measuring the turbidity of said test effluent;
      iv. comparing the turbidity of said test effluent to the turbidity of said calibration effluent, for determining the efficiency of the filter system.

* * * * *